United States Patent [19]
Edwards

[11] Patent Number: 6,044,846
[45] Date of Patent: *Apr. 4, 2000

[54] METHOD TO TREAT ESOPHAGEAL SPHINCTERS

[76] Inventor: Stuart D. Edwards, 658 Westridge Dr., Portola Valley, Calif. 94028

[*] Notice: This patent is subject to a terminal disclaimer.

[21] Appl. No.: 09/032,367

[22] Filed: Feb. 27, 1998

Related U.S. Application Data

[63] Continuation-in-part of application No. 08/731,372, Oct. 11, 1996, Pat. No. 5,964,755, which is a continuation-in-part of application No. 08/319,373, Oct. 6, 1994, Pat. No. 5,575,788, which is a continuation-in-part of application No. 08/286,862, Aug. 4, 1994, Pat. No. 5,588,672, which is a continuation-in-part of application No. 08/272,162, Jul. 7, 1994, Pat. No. 5,569,241, which is a continuation-in-part of application No. 08/265,459, Jun. 24, 1994, Pat. No. 5,505,730.

[51] Int. Cl.$^7$ .................................................... A61B 17/89
[52] U.S. Cl. ......................... 128/898; 606/41; 606/101; 606/133
[58] Field of Search ........................... 606/41, 42, 45–50; 607/100–102, 115, 116, 133; 128/898

[56] References Cited

U.S. PATENT DOCUMENTS

| | | |
|---|---|---|
| 1,798,902 | 3/1931 | Raney . |
| 3,901,241 | 8/1975 | Allen, Jr. . |

(List continued on next page.)

FOREIGN PATENT DOCUMENTS

| | | |
|---|---|---|
| 0 139 607 A1 | 5/1985 | European Pat. Off. . |
| 0 608 609 A2 | 8/1994 | European Pat. Off. . |
| 43 03 882 | 2/1995 | Germany . |
| 3838840 | 2/1997 | Germany . |
| 92/10142 | 6/1992 | WIPO . |
| 93/08755 | 5/1993 | WIPO . |
| 94/10925 | 5/1994 | WIPO . |
| 94/26178 | 11/1994 | WIPO . |
| 95/18575 | 7/1995 | WIPO . |
| 95/19142 | 7/1995 | WIPO . |
| 95/25472 | 9/1995 | WIPO . |
| WO 96 00042 | 1/1996 | WIPO . |
| 96/29946 | 10/1996 | WIPO . |

OTHER PUBLICATIONS

Castell, D. O. "Gastroesophageal Reflux Disease: Current Strategies for Patient Management." *Arch Fam Med.* 5(4): 221–7.

Dallemagne, B., et al. "Laparoscopic Nissen Fundoplication: Preliminary Report." *Surgical Laparoscopy & Endoscopy.* 1991. 1(3): 138–43.

Hinder, R. A., et al. "The Technique of Laparoscopic Nissen Fundoplication." *Surgical Laparoscopy & Endoscopy.* 1992. 1992. 2(3): 265–272.

Karlstrom, L. H. et al. "Ectopic jejunal pacemakers and enterogastric reflux after Roux gastrectomy: Effect of intestinal pacing." *Surgery.* 1989. 106(3): 486–495.

Kelly, K. A., et al. "Duodenal–gastric reflux and slowed gastric emptying by electrical pacing of the canine duodenal pacesetter potential." *Gastroenterology.* 1977. 72(3):429–33.

Reynolds, J. C. "Influence of pathophysiology, severity, and cost on the medical management of gastroesophageal reflux disease." *Am J Health–Syst Pharm.* 53 (22 Suppl 3): S5–12.

(List continued on next page.)

*Primary Examiner*—Michael Peffley
*Attorney, Agent, or Firm*—Ryan Kromholtz & Manion, S.C.

[57] ABSTRACT

A method of treating a sphincter provides a catheter means and an energy delivery device means coupled to the catheter means. The energy delivery device means has a tissue piercing distal end. The catheter means is introduced into an esophagus. A sphincter exterior surface is pierced with the energy delivery device means tissue piercing distal. The energy delivery device means tissue piercing distal end is advanced a sufficient distance in an interior of the sphincter to a tissue site. Energy is controllably delivered to the tissue site. Controlled cell necrosis is created in the sphincter to reduce a frequency of sphincter relaxation.

69 Claims, 13 Drawing Sheets

U.S. PATENT DOCUMENTS

| | | |
|---|---|---|
| 4,011,872 | 3/1977 | Komiya . |
| 4,196,724 | 4/1980 | Wirt et al. . |
| 4,411,266 | 10/1983 | Cosman . |
| 4,423,812 | 1/1984 | Sato . |
| 4,532,924 | 8/1985 | Auth et al. . |
| 4,565,200 | 1/1986 | Cosman . |
| 4,901,737 | 2/1990 | Toone . |
| 4,906,203 | 3/1990 | Margrave et al. . |
| 4,907,589 | 3/1990 | Cosman . |
| 4,943,290 | 7/1990 | Rexroth et al. . |
| 4,947,842 | 8/1990 | Marchosky et al. . |
| 4,966,597 | 10/1990 | Cosman . |
| 4,976,711 | 12/1990 | Parins et al. . |
| 5,035,696 | 7/1991 | Rydell ........ 606/47 |
| 5,046,512 | 9/1991 | Murchie . |
| 5,057,107 | 10/1991 | Parins et al. . |
| 5,078,717 | 1/1992 | Parins et al. . |
| 5,083,565 | 1/1992 | Parins . |
| 5,088,979 | 2/1992 | Filipi et al. ........ 604/26 |
| 5,094,233 | 3/1992 | Brennan . |
| 5,100,423 | 3/1992 | Fearnot . |
| 5,106,360 | 4/1992 | Ishiwara et al. . |
| 5,122,137 | 6/1992 | Lennox . |
| 5,125,928 | 6/1992 | Parins et al. . |
| 5,190,541 | 3/1993 | Abele et al. . |
| 5,197,963 | 3/1993 | Parins . |
| 5,197,964 | 3/1993 | Parins . |
| 5,205,287 | 4/1993 | Erbel et al. . |
| 5,215,103 | 6/1993 | Desai . |
| 5,254,126 | 10/1993 | Filipi et al. . |
| 5,256,138 | 10/1993 | Burek et al. . |
| 5,257,451 | 11/1993 | Edwards et al. . |
| 5,275,162 | 1/1994 | Edwards et al. . |
| 5,275,608 | 1/1994 | Forman et al. . |
| 5,277,201 | 1/1994 | Stern . |
| 5,281,216 | 1/1994 | Klicek . |
| 5,281,217 | 1/1994 | Edwards et al. . |
| 5,281,218 | 1/1994 | Imran . |
| 5,290,286 | 3/1994 | Parins . |
| 5,293,869 | 3/1994 | Edwards et al. . |
| 5,309,910 | 5/1994 | Edwards et al. . |
| 5,313,943 | 5/1994 | Houser et al. . |
| 5,314,466 | 5/1994 | Stern et al. . |
| 5,316,020 | 5/1994 | Truffer . |
| 5,328,467 | 7/1994 | Edwards et al. . |
| 5,334,196 | 8/1994 | Scott et al. . |
| 5,348,554 | 9/1994 | Imran et al. . |
| 5,363,861 | 11/1994 | Edwards et al. . |
| 5,365,926 | 11/1994 | Desai . |
| 5,365,945 | 11/1994 | Halstrom . |
| 5,366,490 | 11/1994 | Edwards et al. . |
| 5,368,557 | 11/1994 | Nita et al. . |
| 5,368,592 | 11/1994 | Stern et al. . |
| 5,370,675 | 12/1994 | Edwards et al. . |
| 5,370,678 | 12/1994 | Edwards et al. . |
| 5,383,876 | 1/1995 | Nardella . |
| 5,383,917 | 1/1995 | Desai . |
| 5,385,544 | 1/1995 | Edwards et al. . |
| 5,397,339 | 3/1995 | Desai . |
| 5,398,683 | 3/1995 | Edwards et al. . |
| 5,401,272 | 3/1995 | Perkins . |
| 5,403,311 | 4/1995 | Abele et al. . |
| 5,409,453 | 4/1995 | Lundquist et al. . |
| 5,421,819 | 6/1995 | Edwards et al. . |
| 5,423,808 | 6/1995 | Edwards et al. . |
| 5,423,811 | 6/1995 | Imran et al. . |
| 5,423,812 | 6/1995 | Ellman et al. . |
| 5,433,739 | 7/1995 | Sluijter et al. . |
| 5,435,805 | 7/1995 | Edwards et al. . |
| 5,441,499 | 8/1995 | Fritzsch . |
| 5,456,662 | 10/1995 | Edwards et al. . |
| 5,456,682 | 10/1995 | Edwards et al. . |
| 5,458,596 | 10/1995 | Lax et al. . |
| 5,458,597 | 10/1995 | Edwards et al. . |
| 5,470,308 | 11/1995 | Edwards et al. . |
| 5,471,982 | 12/1995 | Edwards et al. . |
| 5,472,441 | 12/1995 | Edwards et al. . |
| 5,484,400 | 1/1996 | Edwards et al. . |
| 5,486,161 | 1/1996 | Lax et al. . |
| 5,490,984 | 2/1996 | Freed . |
| 5,496,271 | 3/1996 | Burton et al. ........ 604/54 |
| 5,505,728 | 4/1996 | Ellman et al. . |
| 5,505,730 | 4/1996 | Edwards . |
| 5,507,743 | 4/1996 | Edwards et al. . |
| 5,509,419 | 4/1996 | Edwards et al. . |
| 5,514,130 | 5/1996 | Baker . |
| 5,514,131 | 5/1996 | Edwards et al. . |
| 5,520,684 | 5/1996 | Imran . |
| 5,531,676 | 7/1996 | Edwards et al. . |
| 5,531,677 | 7/1996 | Lundquist et al. . |
| 5,536,240 | 7/1996 | Edwards et al. . |
| 5,536,267 | 7/1996 | Edwards et al. . |
| 5,540,655 | 7/1996 | Edwards et al. . |
| 5,542,915 | 8/1996 | Edwards et al. . |
| 5,542,916 | 8/1996 | Hirsch et al. . |
| 5,545,161 | 8/1996 | Imran . |
| 5,545,171 | 8/1996 | Sharkey et al. . |
| 5,545,193 | 8/1996 | Fleischman et al. . |
| 5,545,434 | 8/1996 | Huarng . |
| 5,549,108 | 8/1996 | Edwards et al. . |
| 5,549,644 | 8/1996 | Lundquist et al. . |
| 5,554,110 | 9/1996 | Edwards et al. . |
| 5,556,377 | 9/1996 | Rosen et al. . |
| 5,558,672 | 9/1996 | Edwards et al. . |
| 5,558,673 | 9/1996 | Edwards et al. . |
| 5,571,116 | 11/1996 | Bolanos et al. . |
| 5,599,345 | 2/1997 | Edwards et al. . |
| 5,609,151 | 3/1997 | Mulier et al. . |
| 5,624,439 | 4/1997 | Edwards et al. . |
| 5,676,674 | 10/1997 | Bolanos et al. . |
| 5,688,490 | 11/1997 | Tournier et al. . |

OTHER PUBLICATIONS

Urschel, J. D. "Complications of Antireflux Surgery." *Am J Surg*. 1993. 166(1): 68–70.

Kaneko, et al., Physiological Laryngeal Pacemaker, May 1985, Trans Am Soc Artif Intern Organs vol. XXXI, pp. 293–296.

Mugica, et al., *Direct Diaphragm Stimulation*, Jan., 1987, PACE, vol. 10, pp. 252–256.

Mugica, et al., *Neurostimulation: An Overview*, Chapter 21, *Preliminary Test of a Muscular Diaphragm Pacing System on Human Patients*, 1985, pp. 263–279.

Nochomovitz, et al., Electrical Activation of the Diaphragm, Jun. 1988, Clinics in Chest Medicine, vol. 9, No. 2, pp. 349–358.

Prior, et al., Treatment of Menorrhagia by Radiofrequency Heating, 1991, Int. J. Hyperthermia, vol. 7, pp. 213–220.

Rice, et al., *Endoscopic Paranasal Sinus Surgery*, Chapters 5, Functional Endoscopic Paranasal Sinus Surgery, The Technique of Messerkling, Raven Press, 1988, pp. 75–104.

Rice, et al., *Endoscopic Paranasal Sinus Surgery*, Chapters 6, Total Endoscopic Sphenoethmoidectomy, The Technique of Wigand, Raven Press, 1988, pp. 105–125.

METHOD TO TREAT ESOPHAGEAL SPHINCTERS

CROSS-RELATED APPLICATIONS

This application is a continuation-in-part of U.S. patent application Ser. No. 08/731,372, filed Oct. 11, 1996, now U.S. Pat. No. 5,964,755, which is a continuation-in-part of U.S. patent application Ser. No. 08/319,373, filed Oct. 6, 1994, now U.S. Pat. No. 5,575,788, which is a continuation-in-part of U.S. application Ser. No. 08/286,862, filed Aug. 4, 1994, now U.S. Pat. No. 5,588,672, which is a continuation-in-part of U.S. patent application Ser. No. 08/272,162, filed Jul. 7, 1994, now U.S. Pat. No. 5,569,241, which is a continuation-in-part of U.S. patent application Ser. No. 08/265,459, filed Jun. 24, 1994, now U.S. Pat. No. 5,505,730, and is related to concurrently filed Application entitled "GERD Treatment Apparatus and Method" identified as U.S. patent application Ser. No. 09/077,238, filed Jan. 14, 1998, all with named inventor Stuart D. Edwards, and all of which are incorporated herein by reference.

FIELD OF THE INVENTION

This invention relates generally to a method to treat sphincters, and more particularly to a method to treat esophageal sphincters.

DESCRIPTION OF RELATED ART

Gastroesophageal reflux disease (GERD) is a common gastroesophageal disorder in which the stomach contents are ejected into the lower esophagus due to a dysfunction of the lower esophageal sphincter (LES). These contents are highly acidic and potentially injurious to the esophagus resulting in a number of possible complications of varying medical severity. The reported incidence of GERD in the U.S. is as high as 10% of the population (Castell DO; Johnston BT: *Gastroesophageal Reflux Disease: Current Strategies For Patient Management*. Arch Fam Med, 5(4):221–7; (1996 April)).

Acute symptoms of GERD include heartburn, pulmonary disorders and chest pain. On a chronic basis, GERD subjects the esophagus to ulcer formation, esophagitis and may result in more severe complications including esophageal obstruction, significant blood loss and perforation of the esophagus. Severe esophageal ulcerations occur in 20–30% of patients over age 65. Moreover, GERD causes adenocarcinoma, or cancer of the esophagus, which is increasing in incidence faster than any other cancer (Reynolds JC: *Influence Of Pathophysiology, Severity, And Cost On The Medical Management Of Gastroesophageal Reflux Disease*. Am J Health Syst Pharm, 53(22 Suppl 3):S5–12 (Nov. 15, 1996)).

Current drug therapy for GERD includes histamine receptor blockers which reduce stomach acid secretion and other drugs which may completely block stomach acid. However, while pharmacologic agents may provide short term relief, they do not address the underlying cause of LES dysfunction.

Invasive procedures requiring percutaneous introduction of instrumentation into the abdomen exist for the surgical correction of GERD. One such procedure, Nissen fundoplication, involves constructing a new "valve" to support the LES by wrapping the gastric fundus around the lower esophagus. Although the operation has a high rate of success, it is an open abdominal procedure with the usual risks of abdominal surgery including: postoperative infection, herniation at the operative site, internal hemorrhage and perforation of the esophagus or of the cardia. In fact, a recent 10 year, 344 patient study reported the morbidity rate for this procedure to be 17% and mortality 1% (Urschel, JD: *Complications Of Antireflux Surgery*, Am J Surg 166(1): 68–70; (1993 July)). This rate of complication drives up both the medical cost and convalescence period for the procedure and may exclude portions of certain patient populations (e.g., the elderly and immuno-compromised).

Efforts to perform Nissen fundoplication by less invasive techniques have resulted in the development of laparoscopic Nissen fundoplication. Laparoscopic Nissen fundoplication, reported by Dallemagne et al. *Surgical Laparoscopy and Endoscopy*, Vol. 1, No. 3, (1991), pp. 138–43 and by Hindler et al. *Surgical Laparoscopy and Endoscopy*, Vol. 2, No. 3, (1992), pp. 265–272, involves essentially the same steps as Nissen fundoplication with the exception that surgical manipulation is performed through a plurality of surgical cannula introduced using trocars inserted at various positions in the abdomen.

Another attempt to perform fundoplication by a less invasive technique is reported in U.S. Pat. No. 5,088,979. In this procedure, an invagination device containing a plurality of needles is inserted transorally into the esophagus with the needles in a retracted position. The needles are extended to engage the esophagus and fold the attached esophagus beyond the gastroesophageal junction. A remotely operated stapling device, introduced percutaneously through an operating channel in the stomach wall, is actuated to fasten the invaginated gastroesophageal junction to the surrounding involuted stomach wall.

Yet another attempt to perform fundoplication by a less invasive technique is reported in U.S. Pat. No. 5,676,674. In this procedure, invagination is done by a jaw-like device and fastening of the invaginated gastroesophageal junction to the fundus of the stomach is done via a transoral approach using a remotely operated fastening device, eliminating the need for an abdominal incision. However, this procedure is still traumatic to the LES and presents the postoperative risks of gastroesophageal leaks, infection and foreign body reaction, the latter two sequela resulting when foreign materials such as surgical staples are implanted in the body.

While the methods reported above are less invasive than an open Nissen fundoplication, some still involve making an incision into the abdomen and hence the increased morbidity and mortality risks and convalescence period associated with abdominal surgery. Others incur the increased risk of infection associated with placing foreign materials into the body. All involve trauma to the LES and the risk of leaks developing at the newly created gastroesophageal junction.

Besides the LES, there are other sphincters in the body which if not functionally properly can cause disease states or otherwise adversely affect the lifestyle of the patient. Reduced muscle tone or otherwise aberrant relaxation of sphincters can result in a laxity of tightness disease states including but not limited to urinary incontinence.

There is a need to provide a method to treat a sphincter and reduce a frequency of sphincter relaxation. Another need exists for a method to create controlled cell necrosis in a sphincter tissue underlying a sphincter mucosal layer. Yet another need exists for a method to create controlled cell necrosis in a sphincter and minimize injury to a mucosal layer of the sphincter. There is another need for a method to controllably produce a lesion in a sphincter without creating a permanent impairment of the sphincter's ability to achieve a physiologically normal state of closure. Still a further need exists for a method to create a tightening of a sphincter without permanently damaging anatomical structures near the sphincter. There is still another need for a method to create controlled cell necrosis in a lower esophageal sphincter to reduce a frequency of reflux of stomach contents into an esophagus.

SUMMARY OF THE INVENTION

Accordingly, an object of the present invention is to provide a method to treat a sphincter and reduce a frequency of sphincter relaxation.

Another object of the invention is to provide a method to create controlled cell necrosis in a sphincter tissue underlying a sphincter mucosal layer.

Yet another object of the invention is to provide a method to create controlled cell necrosis in a sphincter and minimize injury to a mucosal layer of the sphincter.

A further object of the invention is to provide a method to controllably produce a lesion in a sphincter without creating a permanent impairment of the sphincter's ability to achieve a physiologically normal state of closure.

Still another object of the invention is to provide a method to create a tightening of a sphincter without permanently damaging anatomical structures near the sphincter.

Another object of the invention is to provide a method to create controlled cell necrosis in a lower esophageal sphincter to reduce a frequency of reflux of stomach contents into an esophagus.

These and other objects of the invention are provided in a method of treating a sphincter that provides a catheter means and an energy delivery device means coupled to the catheter means. The energy delivery device means has a tissue piercing distal end. The catheter means is introduced into an esophagus. A sphincter exterior surface is pierced with the energy delivery device means tissue piercing distal. The energy delivery device means tissue piercing distal end is advanced a sufficient distance in an interior of the sphincter to a tissue site. Energy is controllably delivered to the tissue site. Controlled cell necrosis is created in the sphincter to reduce a frequency of sphincter relaxation.

In another embodiment of a method to treat the sphincter, a catheter means and an energy delivery device means coupled to the catheter means are provided. The energy delivery device means has an energy delivery surface means sized to be positioned on a tissue surface of the sphincter. The catheter means is introduced into the esophagus. The energy delivery surface means is positioned on the tissue surface of the sphincter. Energy is controllably delivered to the sphincter. Controlled cell necrosis is created of the sphincter to reduce a frequency of sphincter relaxation.

In yet another embodiment of a method to treat the sphincter, a catheter means and an energy delivery device means coupled to the catheter means are provided. The energy delivery device means includes an energy delivery surface means sized to be distanced from a tissue surface of the sphincter while controllably delivering energy to the sphincter. The catheter means is introduced into the esophagus. The energy delivery surface means is distanced from a selected tissue surface of the sphincter. Energy is controllably delivered to the sphincter. Controlled cell necrosis of the sphincter is created to reduce a frequency of sphincter relaxation.

DETAILED DESCRIPTION

Figure 1:
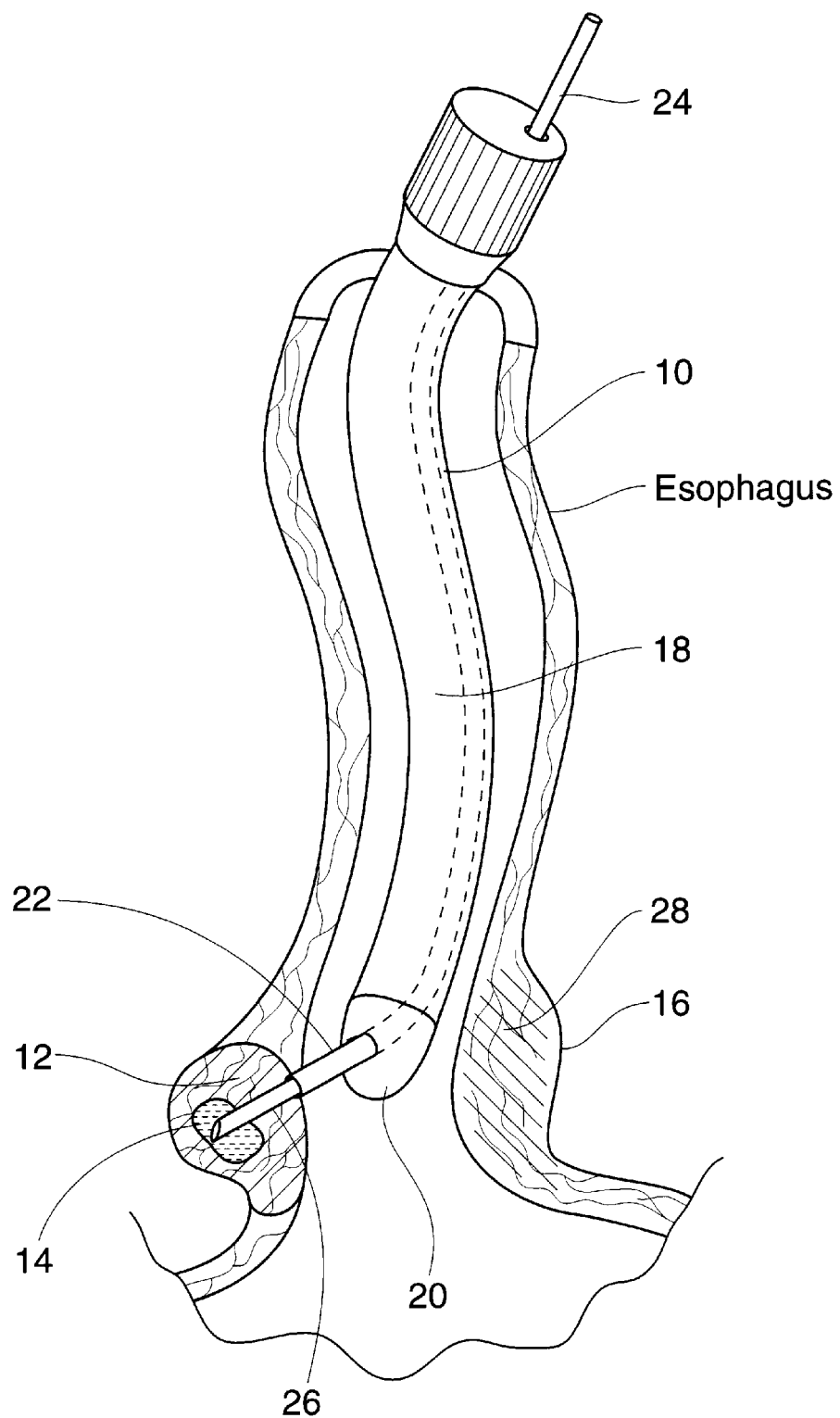
FIG. 1 is an illustrated lateral view of the upper GI tract illustrating the positioning of the sphincter treatment apparatus of the present invention in the lower esophageal sphincter.
Figure 2:
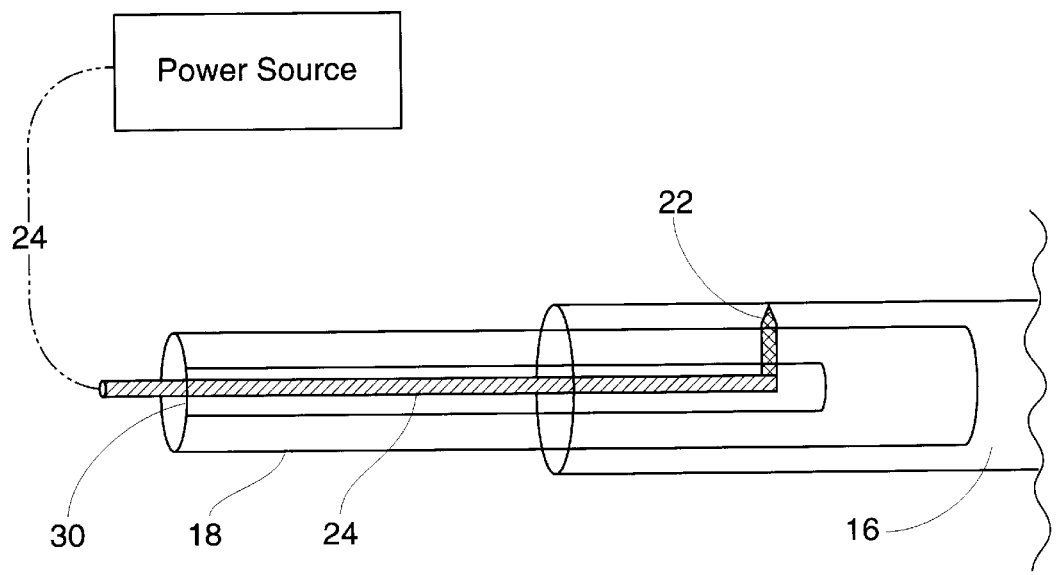
FIG. 2 is a lateral view of the present invention illustrating the catheter lumen, catheter end energy delivery device, cable and power supply.

Referring now to FIGS. 1 and 2, one embodiment of a sphincter treatment apparatus 10 delivers energy to a target tissue site 12 to produce cell necrosis 14 in a sphincter 16, such as the lower esophageal sphincter (LES). In this embodiment, sphincter treatment apparatus 10 comprises a flexible elongate shaft 18, also called catheter 18, with a distal extremity 20, also called catheter end 20, in turn coupled with one or more energy delivery devices 22. Energy delivery devices 22 are coupled to a cable 24 and are also configured to be coupled to a power source. Energy delivery device 22 includes a tissue piercing distal end 26 which is configured to penetrate a fixed depth into a sphincter wall 28 and deliver energy to a portion thereof. In another embodiment, energy delivery device 22 is configured to contact the surface of sphincter wall 28 and deliver energy without penetration of sphincter 16. In still another embodiment, energy delivery device 22 is configured to deliver energy without contact with sphincter wall 28.

Catheter end 20 is configured to be positionable in a sphincter 16 such as the LES or adjacent anatomical structure, such as the cardia of the stomach. Catheter 18 has sufficient length to position catheter end 20 in the LES and/or stomach using a trans-oral approach. Typical lengths for catheter 18 include, but are not limited to, a range of 40–180 cms. Suitable materials for catheter 18 include, but are not limited to, polyethylenes, polyurethanes, silicones and other biocompatible polymers known to those skilled in the art. Catheter 18 may have one or more lumens 30, that extend the full length of catheter 18, or only a portion thereof Lumens 30 may be used as paths for cables, catheters, guide wires, pull wires, insulated wires, fluid and optical fibers. Energy delivery devices 22 can be in the form of needle electrodes, both solid or hollow, as is well known to those skilled in the art. In other embodiments, energy delivery device 22 can be conical, cylindrical, rectangular or any polyhedron; each of said shapes having a flat, rounded, beveled, or pointed tip. Suitable materials for energy delivery device 22 include a combination of one or more of the following: i) stainless and other steels suitable for electrode applications known to those skilled in the art, ii) alloys of gold, silver and platinum, iii) nickel-titanium alloys, or iv) other conductors known to those skilled in the art.

Cable 24 is configured to facilitate the positioning of energy delivery device 22 a selectable distance (1–4 mms) into the sphincter wall 28. Suitable materials and components for cable 24 include an insulated wire, an insulated guide wire, a plastic-coated stainless steel hypotube with internal wiring, or a catheter with internal wiring, all of which are known to those skilled in the art.

Turning now to a discussion of energy-tissue interactions, energy flowing through sphincter or other tissue causes heating of the tissue due to absorption of the energy by the tissue. This heating can cause injury to the affected cells and can be substantial enough to cause cell death, a phenomenon also known as cell necrosis. The controlled delivery of energy by energy delivery device 22 results in controlled cell necrosis, or lesions 14 at target tissue site 12.

Suitable energy devices and power sources for energy delivery device 22 include the following: (i) a radio-frequency (RF) source coupled to an RF electrode, (ii) a coherent source of light coupled to an optical fiber, (iii) an incoherent light source coupled to an optical fiber, (iv) a heated fluid coupled to a catheter with a closed channel configured to receive the heated fluid, (v) a heated fluid coupled to a catheter with an open channel configured to receive the heated fluid, (vi) a cooled fluid coupled to a catheter with a closed channel configured to receive the cooled fluid, (vii) a cooled fluid coupled to a catheter with an open channel configured to receive the cooled fluid, (viii) a cryogenic fluid, (ix) a resistive heating source, (x) a microwave source providing energy from 915 MHz to 2.45 GHz and coupled to a microwave antenna, (xi) an ultrasound power source coupled to an ultrasound emitter, wherein the ultrasound power source produces energy in the range of 300 KHZ to 3 GHz, or (xii) combinations of any of the above. For ease of discussion for the remainder of this application, the power source utilized is an RF source and energy delivery device 22 is one or more RF electrodes 22, also described as electrodes 22. However, all of the other herein mentioned power sources and energy delivery devices are equally applicable to sphincter treatment apparatus 10.

Figure 3:
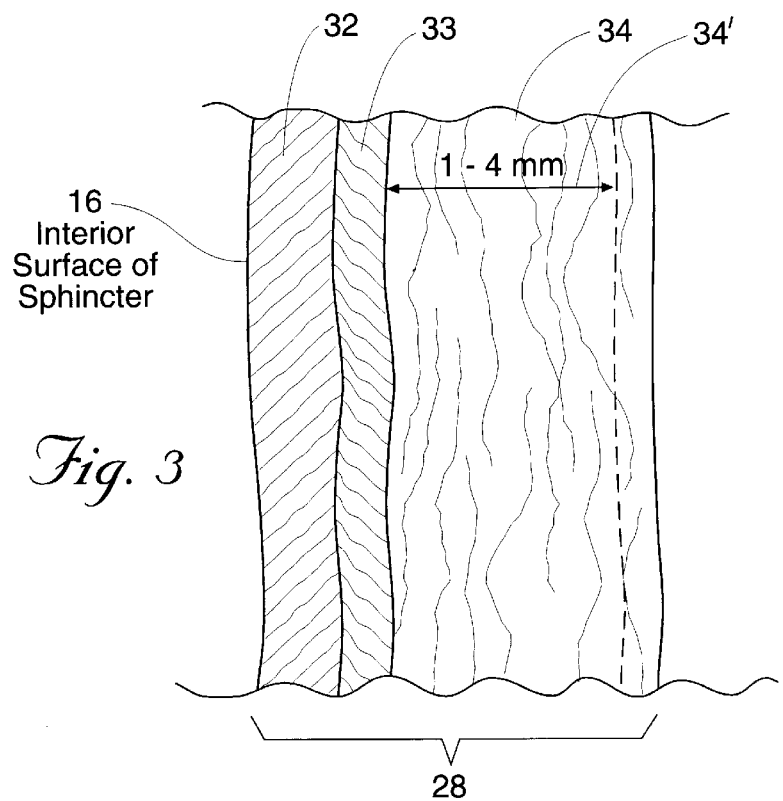
FIG. 3 depicts a cross sectional view of sphincter anatomy illustrating the layers of the sphincter wall.

Turning now to a discussion of sphincter anatomy (depicted in FIG. 3), the first several layers of sphincter 16 consist of a mucosal layer 32, a submucosal layer 33 and an underlying smooth muscle layer 34. RF electrode 22 is configured to produce controlled cell necrosis or lesions 14 in smooth muscle tissue layer 34 underlying mucosal and submucosal layers 32 and 33. More specifically, RF electrode 22 is configured to produce controlled cell necrosis 14 in the portion of smooth muscle tissue 34' that lies approximately 1–4 mms from the surface of mucosal layer 32.

Figure 4:
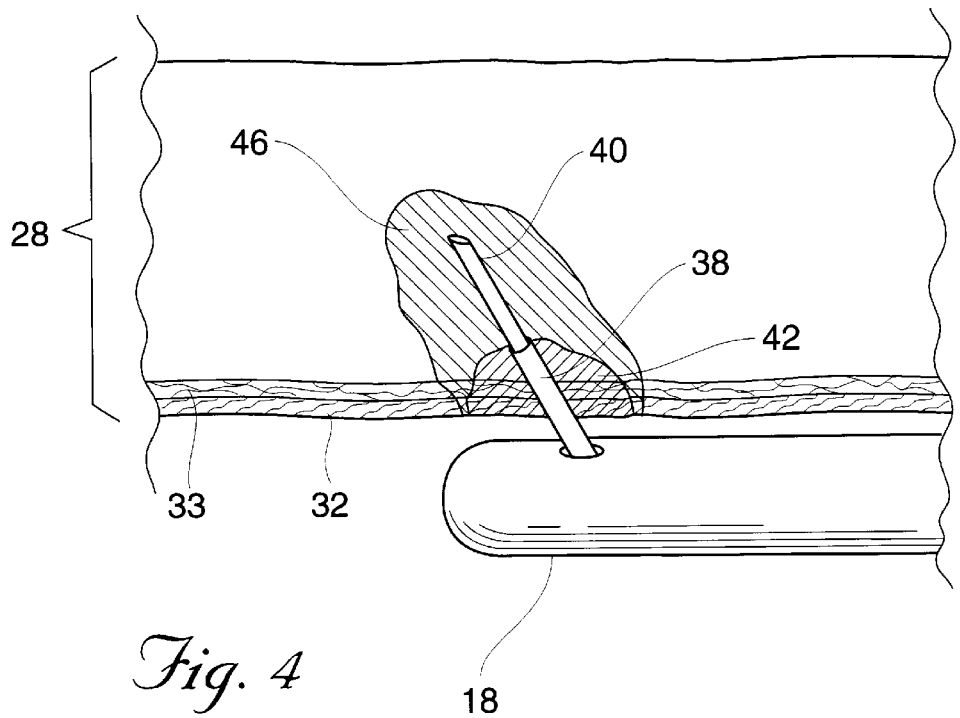
FIG. 4 is a lateral view of the RF electrode and sphincter wall, illustrating insulated and exposed electrode segments and the creation of a protected site.

Referring now to FIG. 4, RF electrode 22 has an insulator 36, covering the exterior of an insulated segment 38 except for an exposed segment 40. For purposes of this disclosure, an insulator is a barrier to either thermal or electromagnetic energy flow. As shown in FIG. 4, insulated segment 38 is of sufficient length to extend into sphincter wall 28 and minimize the transmission of energy and subsequent injury to a protected site 42 near or adjacent to insulated segment 38. Typical lengths for insulated segment 38 include, but are not limited to, 1–4 mms. Suitable materials for insulating mean 36 include, but are not limited to, polytetrafluoroethylene (Teflon®), polyimides, polyamides and other insulating polymers known to those skilled in the art.

Figure 5:
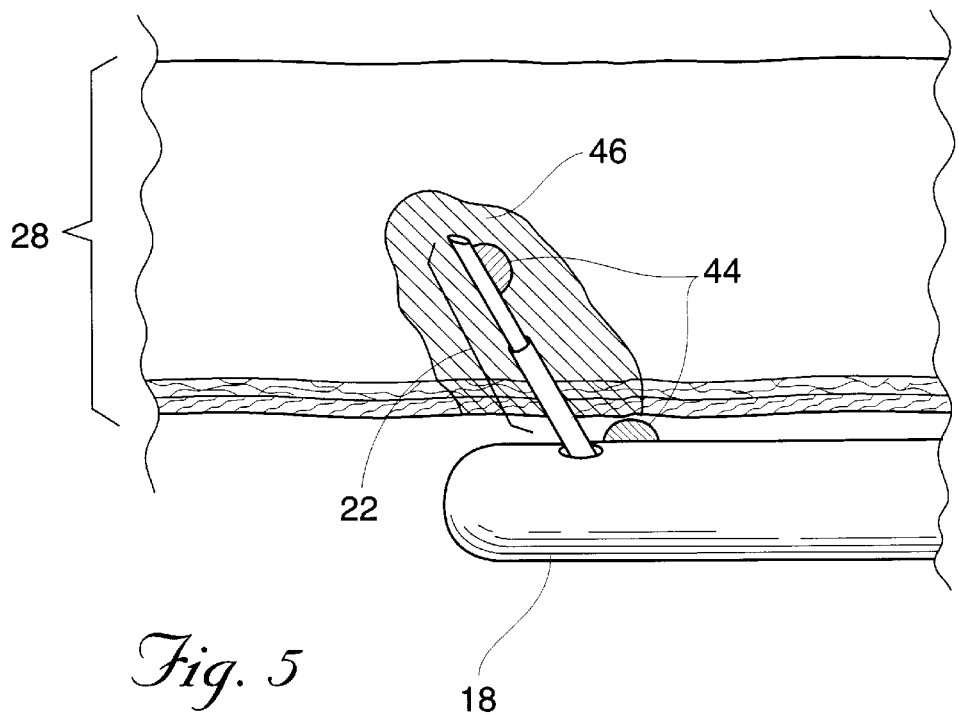
FIG. 5 is an enlarged lateral view illustrating the placement of sensors on/adjacent the energy delivery device/RF electrode.

Referring now to FIG. 5, one or more sensors 44 can be coupled to RF electrode 22 for sensing the temperature of sphincter tissue at target tissue site 12. More specifically, sensors 44 permit accurate determination of the surface temperature of sphincter wall 28 at an electrode tissue interface 46. This information can be used to regulate both the delivery of energy and cooling medium to the interior surface of sphincter wall 28 as will be discussed herein. Sensors 44 can be positioned on or adjacent to RF electrode 22. Suitable sensors that may be used for sensor 44 include: thermocouples, fiber optics, resistive wires, thermocouple IR detectors, and the like. Suitable thermocouples for sensor 44 include: T type with copper constantene, J type, E type and K types as are well known those skilled in the art.

Figure 6:
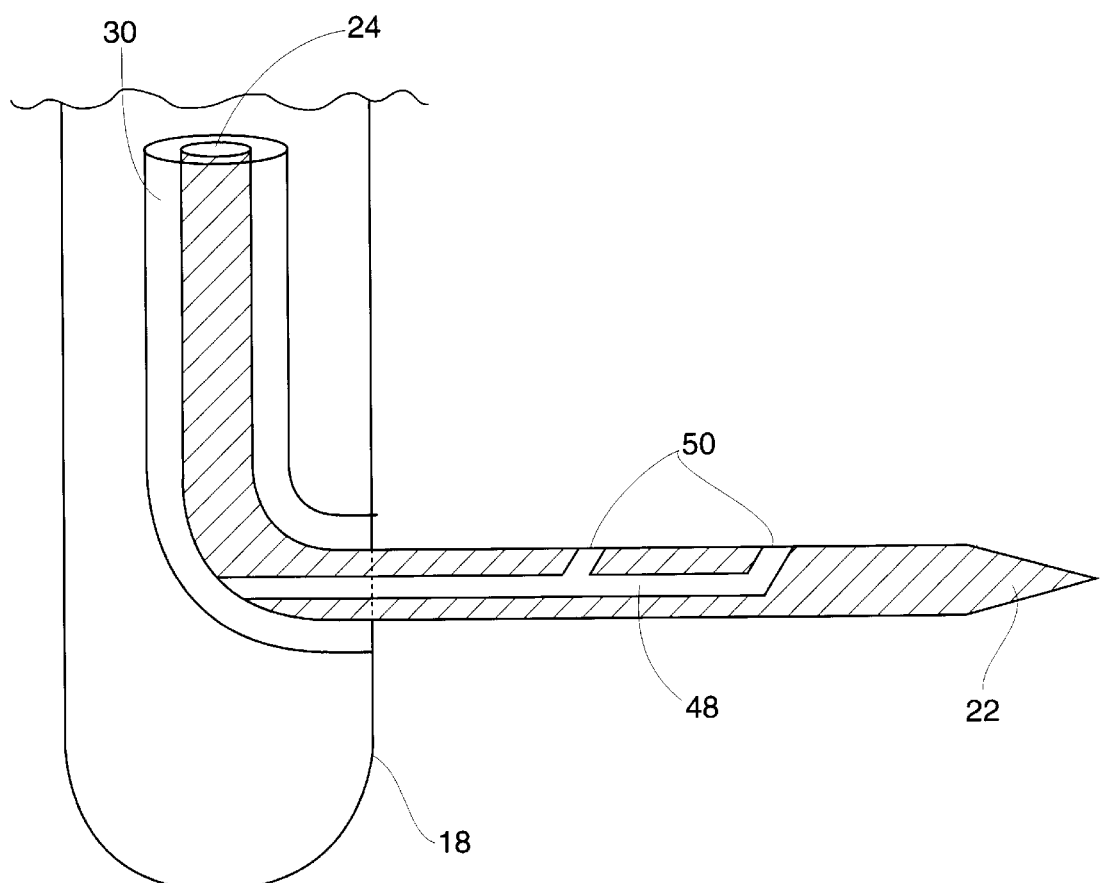
FIG. 6 is a cross sectional view illustrating the use of a fluid introduction lumen and aperture in the energy delivery device/RF electrode for delivery of a cooling medium.

Referring now to FIG. 6, RF electrode 22 includes a fluid introduction lumen 48, that may be coupled with catheter lumen 30. These coupled lumens provide a path for the delivery of a fluid, such as a cooling or electrolytic fluid (which will be discussed herein), to electrode tissue interface 46 or another site. As shown in FIG. 6, fluid introduction lumen 48 may include an aperture 50 on the distal portion of RF electrode 22.

Figure 7:
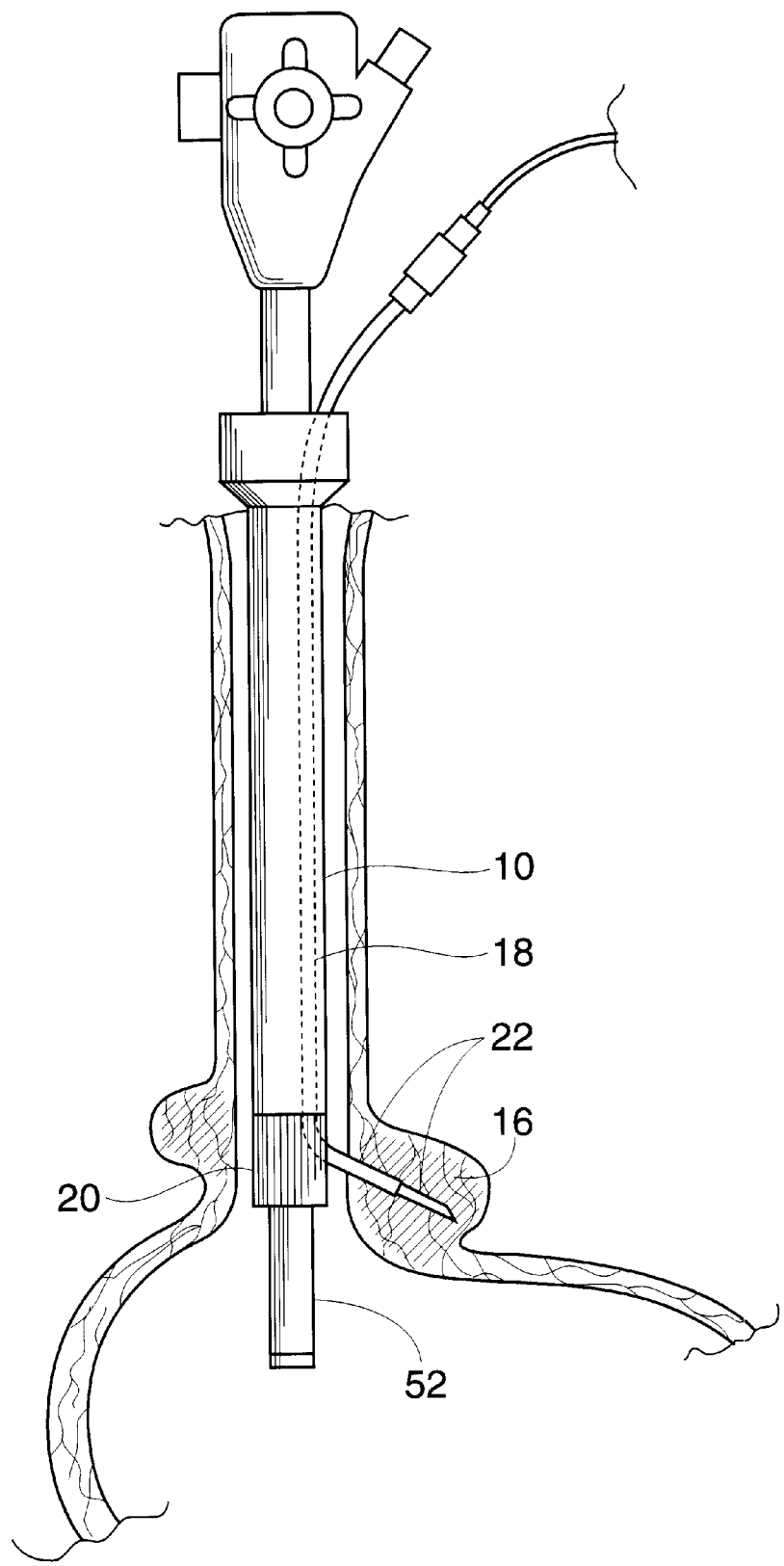
FIG. 7 is a cross sectional view illustrating a visualization device coupled to an embodiment of the invention.

Referring now to FIG. 7, another embodiment of sphincter treatment apparatus 10 includes a visualization device 52 which can include a combination of one or more of the following: a viewing scope, an expanded eyepiece, fiber optics (both imaging and illuminating fibers), video imaging and the like.

Figure 8:
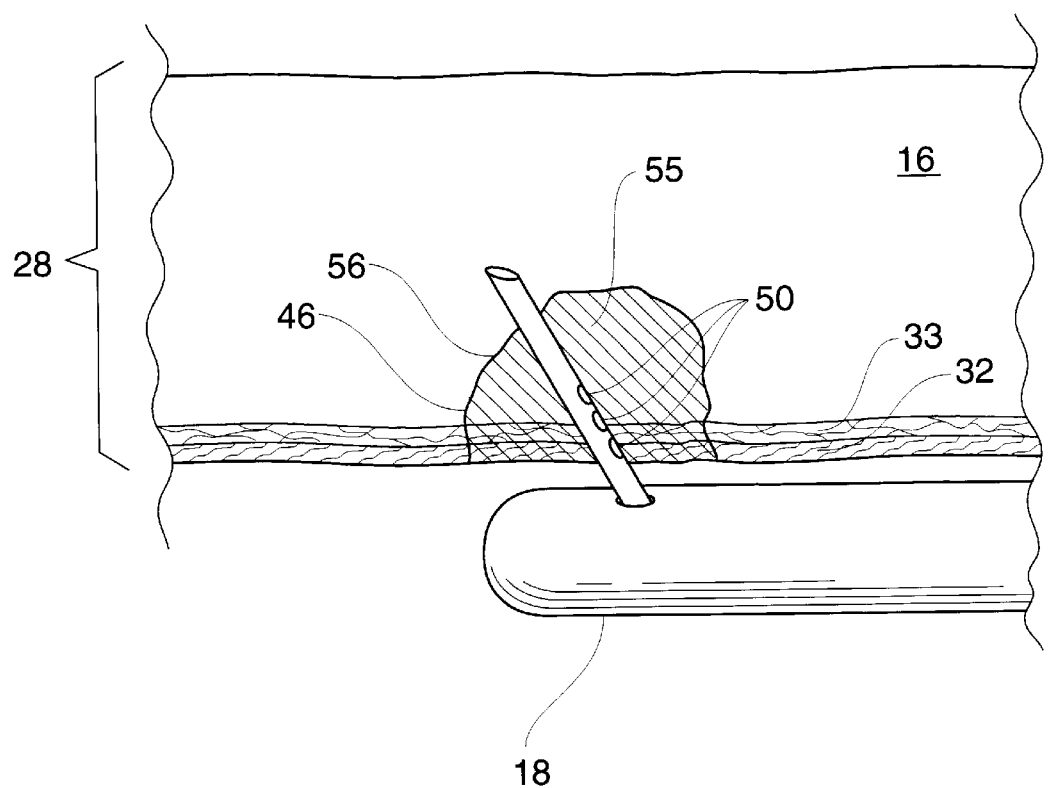
FIG. 8 is a lateral view of the sphincter wall illustrating the use of cooling medium to create cooled zones at the electrode-tissue interface.
Figure 9:
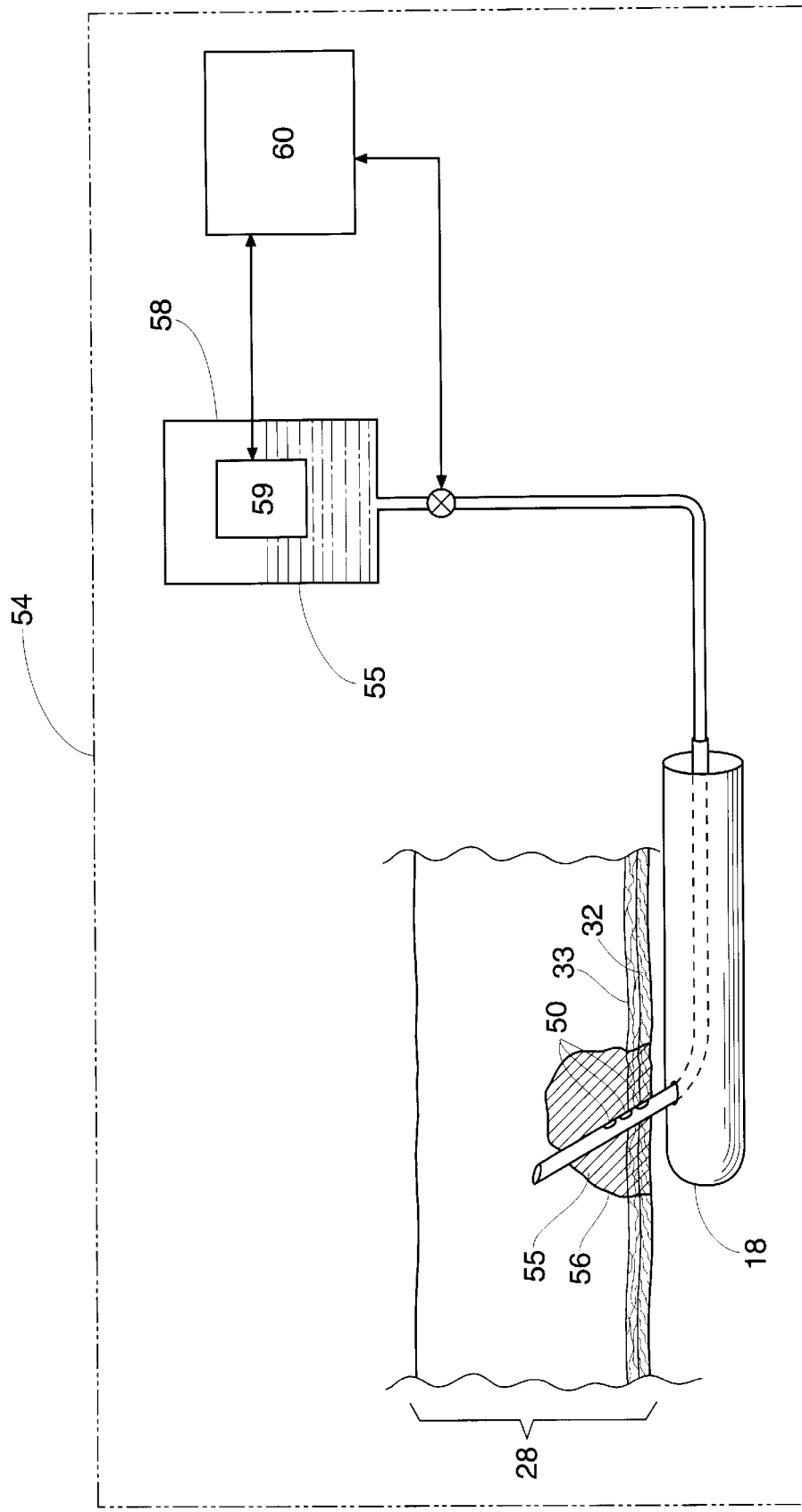
FIG. 9 depicts the flow path and fluid connections employed to deliver cooling medium to the energy delivery device/RF electrode and/or electrodetissue interface.

It may be desirable to employ a cooling system 54 coupled to energy delivery device 22 to cool all or a portion of energy-delivery device 22 and the area near electrode tissue interface 46 before, during or after the delivery of energy in order to reduce the degree and area of cell injury in the tissue adjacent electrode tissue interface 46. As shown in FIG. 8, the use of cooling protects against, or otherwise reduces the degree of, cell damage to cooled zone 56 in the vicinity of aperture 50 and/or electrode tissue interface 46 which will preferably include mucosal and submucosal layers 32 and 33. In one embodiment shown in FIG. 9, cooling system 54 can include one or more of the following: i) a cooling medium 55 (which can be a liquid or a gas) that is delivered to RF electrode 22 via aperture 50 and flow-controlled via a feedback control system 60 discussed herein, ii) a cooling medium reservoir 58 coupled to aperture 50, and iii) a cooling device 59 (which may be integral to fluid reservoir 58) coupled to cooling medium 55 and controlled via a feedback control system 60 discussed herein. In another embodiment, cooling medium 55 can be introduced via apertures 50 or semipermeable membranes located in one or more locations on sphincter treatment apparatus 10 in communication with reservoir 58 and thermal communication with cooling device 59. In yet another embodiment, cooling medium 55 can be introduced externally to RF electrode 22. In still another embodiment, cooling medium 55 is thermally coupled to RF electrode 22 and/or electrode tissue interface 46. In yet another embodiment, cooling device 59 (such as a Peltier effect device or heat pipe) is thermally coupled to RF electrode 22 and/or electrode tissue interface 46.

Figure 10:
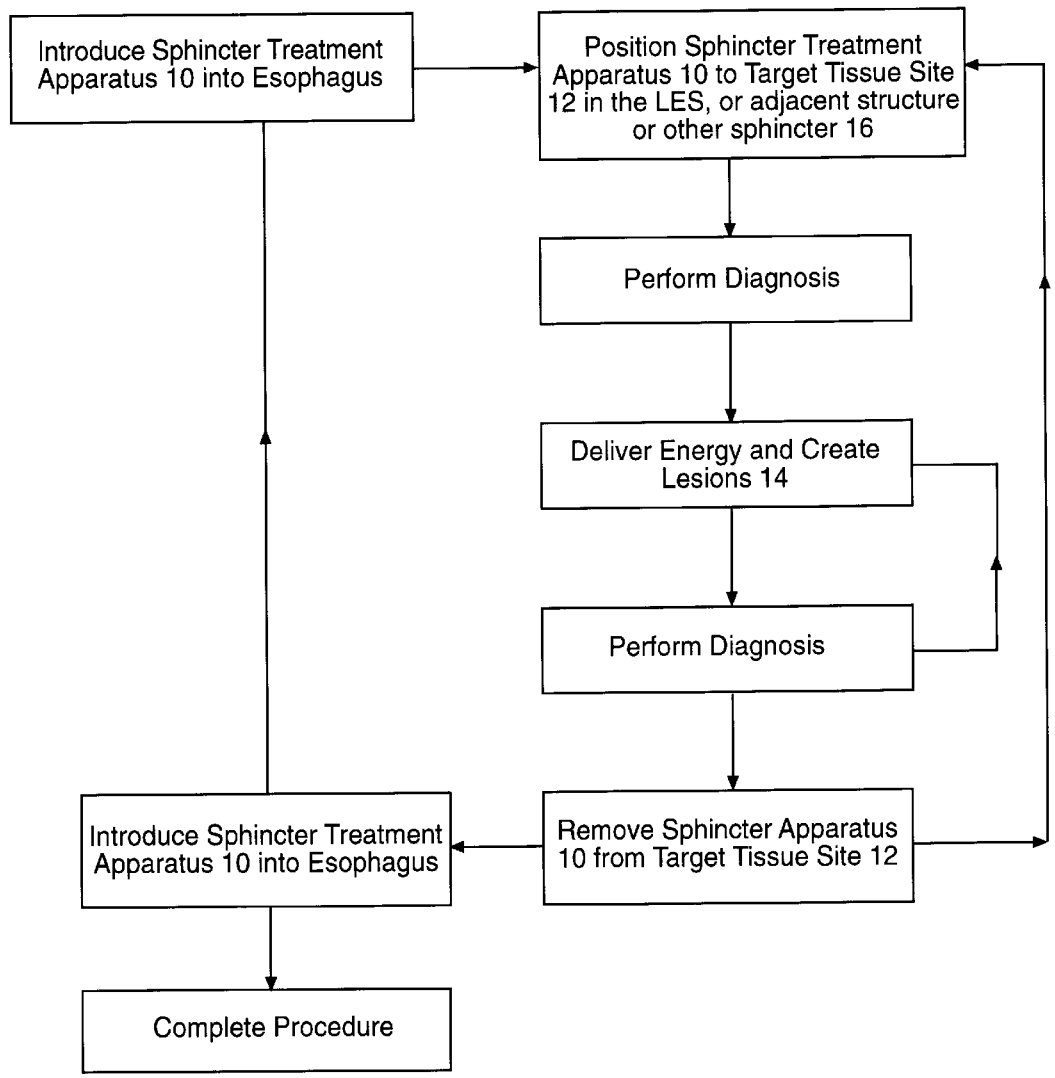
FIG. 10 is a flow chart illustrating a sphincter treatment method.

FIG. 10 is a flow chart illustrating one embodiment of the method for using sphincter treatment apparatus 10. In this embodiment, sphincter treatment apparatus 10 is first introduced into the esophagus under local anesthesia and positioned at target tissue site 12. Sphincter treatment apparatus 10 can be introduced into the esophagus by itself or through a lumen in an endoscope (not shown), such as disclosed in U.S. Pat. Nos. 5,448,990 and 5,275,608, incorporated herein by reference, or a similar esophageal access device known to those skilled in the art.

Figure 11:
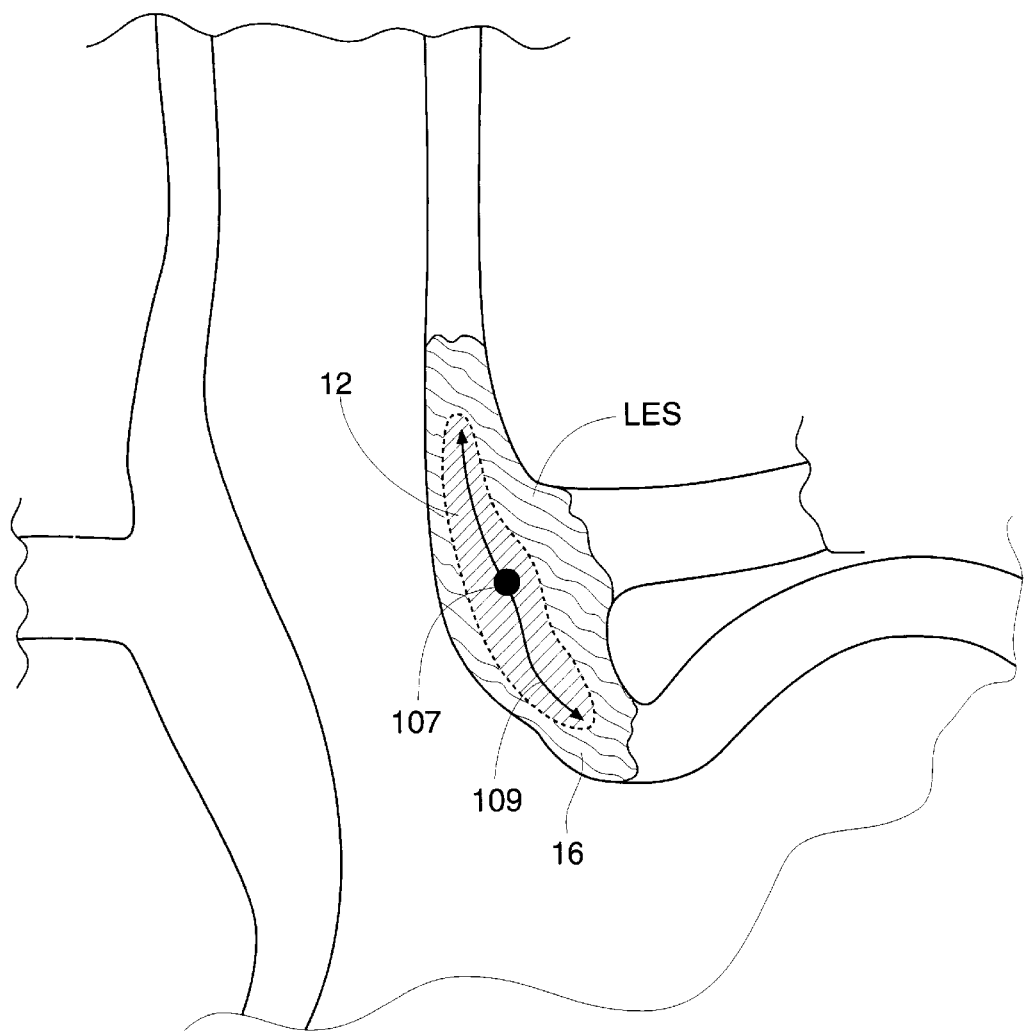
FIG. 11 is a lateral view of sphincter smooth muscle tissue illustrating electrical foci and electrically conductive pathways for the origination and conduction of aberrant electrical signals in the smooth muscle of the lower esophageal sphincter or other tissue.

The diagnostic phase of the procedure then begins and can be performed using a variety of diagnostic methods, including, but not limited to, the following: (i) visualization of the interior surface of the esophagus via an endoscope or other viewing apparatus inserted into the esophagus, (ii) visualization of the interior morphology of the esophageal wall using ultrasonography to establish a baseline for the tissue to be treated, (iii) impedance measurement to determine the electrical conductivity between the esophageal mucosal layers and sphincter treatment apparatus 10, and (iv) measurement and surface mapping of the electropotential of the LES during varying time periods which may include such events as depolarization, contraction and repolarization of LES smooth muscle tissue. This latter technique is done to determine target tissue sites 12 in the LES or adjoining anatomical structures that are acting as electrical foci 107 or electrically conductive pathways 109 for abnormal or inappropriate polarization and relaxation of the smooth muscle of the LES (Refer to FIG. 11).

After diagnosis, the treatment phase of the procedure then begins. In this phase of the procedure the delivery of energy to target tissue site 12 can be conducted under feedback control (described herein), manually or by a combination of both. Feedback control enables sphincter treatment apparatus 10 to be positioned and retained in the esophagus during treatment with minimal attention by the physician. Feedback can be included and is achieved by the use of one or more of the following methods: (i) visualization, (ii) impedance measurement, (iii) ultrasonography, (iv) temperature measurement and, (v) sphincter contractile force measurement via manometry. A second diagnostic phase may be included after the treatment is completed. This provides an indication of LES tightening treatment success, and whether or not a second phase of treatment, to all or only a portion of the esophagus, now or at some later time, should be conducted. The second diagnostic phase is accomplished through, (i) visualization, (ii) measuring impedance, (iii) ultrasonography, (iv) temperature measurement, or (v) measurement of LES tension and contractile force via manometry. It will be appreciated that the above procedure is applicable in whole or part to the treatment of other sphincters in the body.

Figure 12:
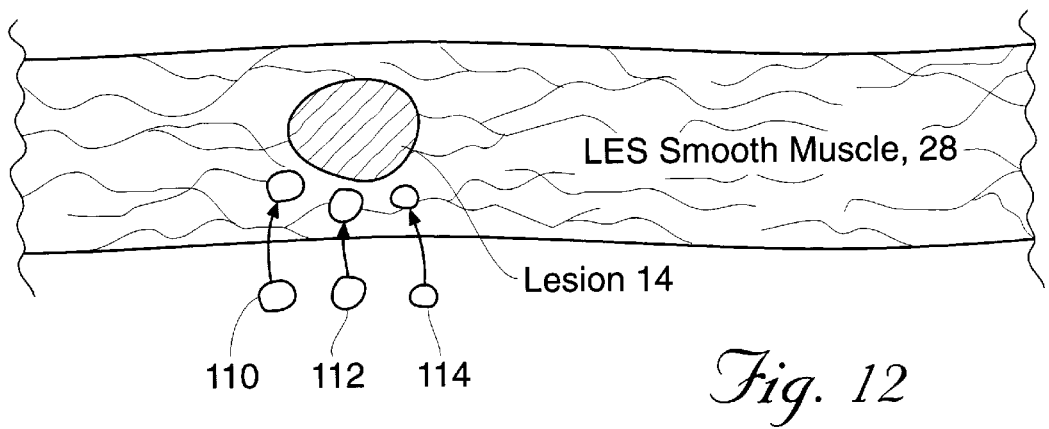
FIG. 12 is a lateral view of a sphincter wall illustrating the infiltration of tissue healing cells into a lesion in the smooth tissue of a sphincter following treatment with the sphincter treatment apparatus of the present invention.
Figure 13:
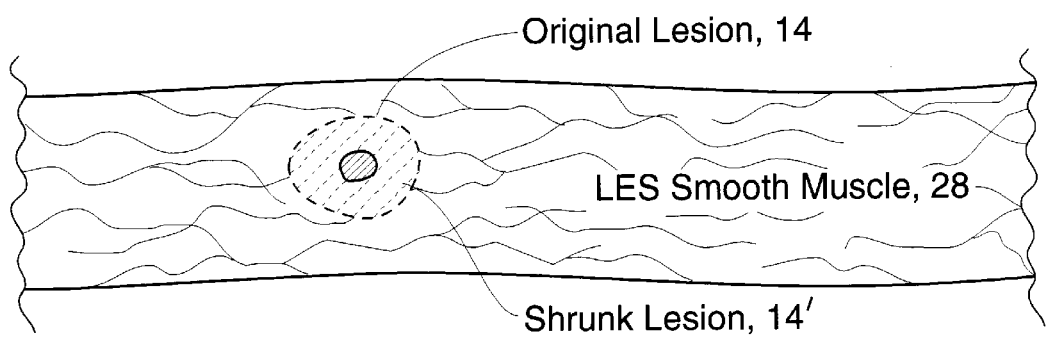
FIG. 13 is a view similar to that of FIG. 12 illustrating shrinkage of the lesion site caused by cell infiltration.

The area and magnitude of cell injury in the LES or sphincter 16 can vary. However, it is desirable to deliver sufficient energy to the targeted tissue site 12 to be able to achieve tissue temperatures in the range of 55–95° C. and produce lesions 14 at depths ranging from 1–4 mms from the interior surface of the LES or sphincter wall 28. It is also desirable to deliver sufficient energy such that the resulting lesions 14 have a sufficient magnitude and area of cell injury to cause an infiltration and/or proliferation of lesion 14 by fibroblasts 110, myofibroblasts 112, macrophages 114 and other cells involved in the tissue healing process (refer to FIG. 12). As shown in FIG. 13, these cells cause a contraction of tissue around lesion 14, decreasing its volume and/or altering the biomechanical properties at lesion 14 so as to result in a tightening of LES or sphincter 16. These changes are reflected in transformed lesion 14' shown in FIG. 13.

Figure 14:
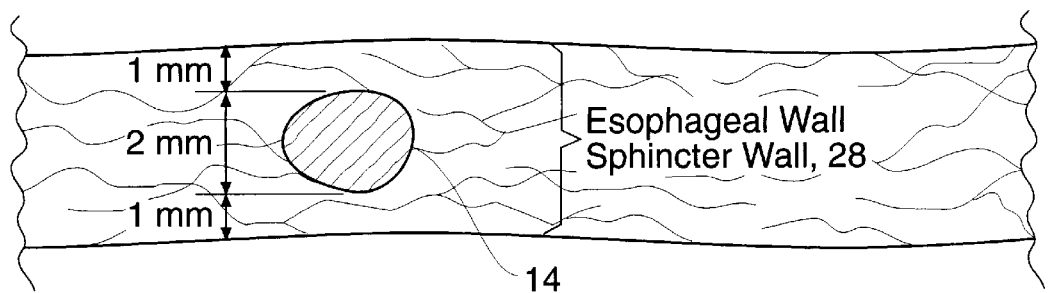
FIG. 14 is a lateral view of the esophageal wall illustrating the preferred placement of lesions in the smooth muscle layer of an esophageal sphincter.

It is desirable that lesions 14 are predominantly located in the smooth muscle layer of selected sphincter 16 at the depths ranging from 1 to 4 mms from the interior surface of sphincter wall 28. Accordingly, the diameter of lesions 14 can vary between 0.1 to 4 mms. It is preferable that lesions 14 are less than 4 mms in diameter in order to reduce the risk of thermal damage to the mucosal layer. In one embodiment, a 2 mm diameter lesion 14 centered in the wall of the smooth muscle provides a 1 mm buffer zone to prevent damage to the mucosa, submucosa and adventitia, while still allowing for cell infiltration and subsequent sphincter tightening on approximately 50% of the thickness of the wall of the smooth muscle (refer to FIG. 14). Also, lesions 14 can vary both in number and position within sphincter wall 28. Once treatment is completed, sphincter treatment apparatus 10 is withdrawn from the esophagus or other sphincter 16. This results in the LES or other sphincter returning to approximately its pretreatment state and diameter.

Figure 15:
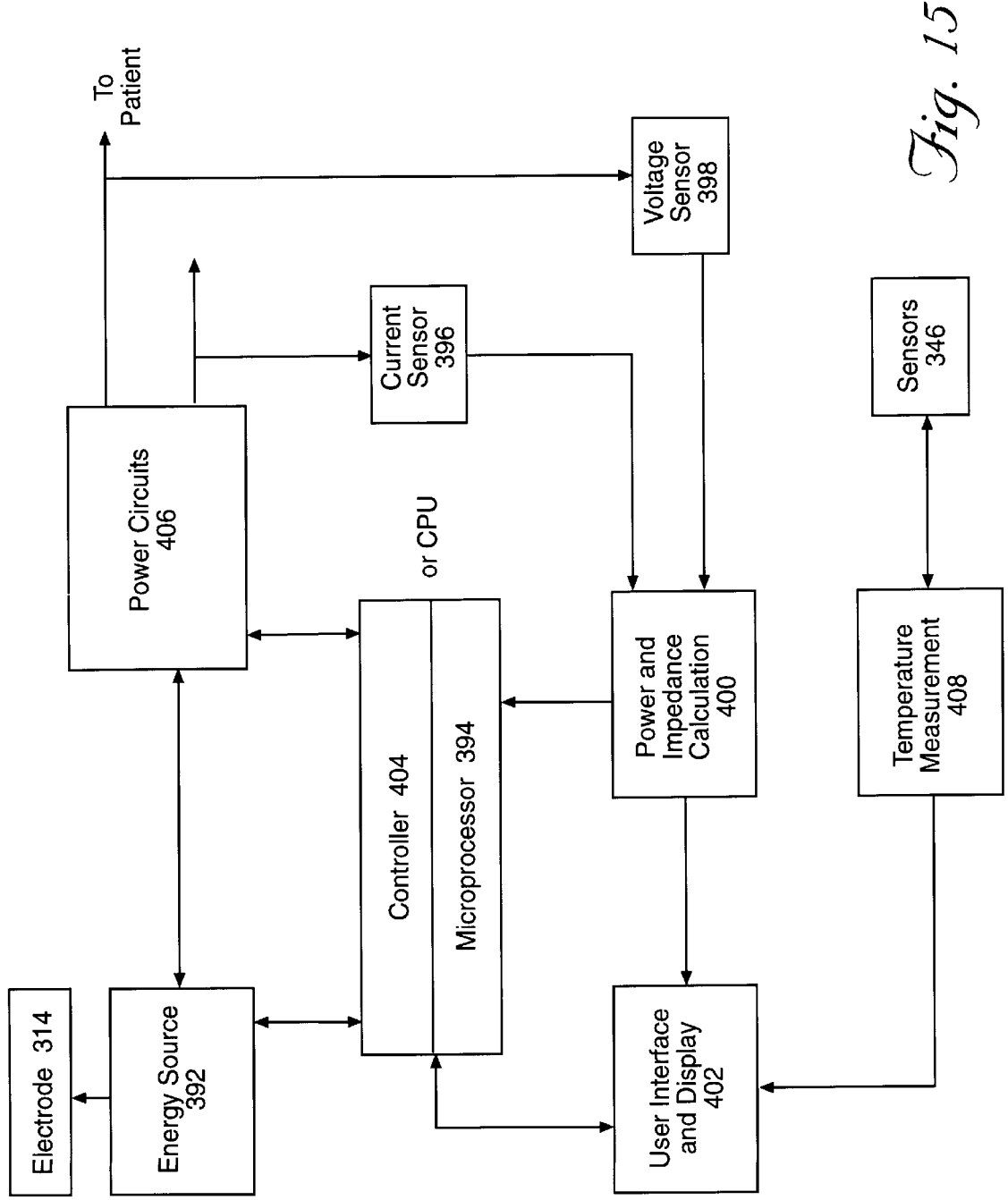
FIG. 15 depicts a block diagram of the feed back control system that can be used with the sphincter treatment apparatus.

In one embodiment, elements of sphincter treatment apparatus 10 are coupled to an open or closed loop feedback control system 60. Referring now to FIG. 15, an open or closed loop feedback system 60 couples sensor 346 to energy source 392. In this embodiment, electrode 314 is one or more RF electrodes 314. The temperature of the tissue, or of RF electrode 314, is monitored, and the output power of energy source 392 adjusted accordingly. The physician can, if desired, override the closed or open loop system 60. A microprocessor 394 can be included and incorporated in the closed or open loop system to switch power on and off, as well as modulate the power. The closed loop system 60 utilizes microprocessor 394 to serve as a controller, monitor the temperature, adjust the RF power, analyze the result, refeed the result, and then modulate the power.

With the use of sensor 346 and feedback control system 60, tissue adjacent to RF electrode 314 can be maintained at a desired temperature for a selected period of time without causing a shut down of the power circuit to electrode 314 due to the development of excessive electrical impedance at electrode 314 or adjacent tissue as is discussed herein. Each RF electrode 314 is connected to resources which generate an independent output. The output maintains a selected energy at RF electrode 314 for a selected length of time.

Current delivered through RF electrode 314 is measured by current sensor 396. Voltage is measured by voltage sensor 398. Impedance and power are then calculated at power and impedance calculation device 400. These values can then be displayed at user interface and display 402. Signals representative of power and impedance values are received by a controller 404.

A control signal is generated by controller 404 that is proportional to the difference between an actual measured value, and a desired value. The control signal is used by power circuits 406 to adjust the power output an appropriate amount in order to maintain the desired power delivered at respective RF electrodes 3 14.

In a similar manner, temperatures detected at sensor 346 provide feedback for maintaining a selected power. Temperature at sensor 346 is used as a safety means to interrupt the delivery of power when maximum pre-set temperatures are exceeded. The actual temperatures are measured at temperature measurement device 408, and the temperatures are displayed at user interface and display 402. A control signal is generated by controller 404 that is proportional to the difference between an actual measured temperature and a desired temperature. The control signal is used by power circuits 406 to adjust the power output an appropriate amount in order to maintain the desired temperature delivered at the sensor 346. A multiplexer can be included to measure current, voltage and temperature, at the sensor 346, and energy can be delivered to RF electrode 314 in monopolar or bipolar fashion.

Controller 404 can be a digital or analog controller, or a computer with software. When controller 404 is a computer it can include a CPU coupled through a system bus. This system can include a keyboard, a disk drive, or other non-volatile memory systems, a display, and other peripherals, as are known in the art. Also coupled to the bus is a program memory and a data memory.

User interface and display 402 includes operator controls and a display.

Controller 404 can be coupled to imaging systems including, but not limited to, ultrasound, CT scanners, X-ray, MRI, mammographic X-ray and the like. Further, direct visualization and tactile imaging can be utilized.

The output of current sensor 396 and voltage sensor 398 are used by controller 404 to maintain a selected power level at RF electrode 314. The amount of RF energy delivered controls the amount of power. A profile of the power delivered to electrode 314 can be incorporated in controller 404 and a preset amount of energy to be delivered may also be profiled.

Circuitry, software and feedback to controller 404 result in process control, the maintenance of the selected power setting which is independent of changes in voltage or current, and is used to change the following process variables: (i) the selected power setting, (ii) the duty cycle (e.g., on-off time), (iii) bipolar or monopolar energy delivery; and, (iv) fluid delivery, including flow rate and pressure. These process variables are controlled and varied, while maintaining the desired delivery of power independent of changes in voltage or current, based on temperatures monitored at sensor 346.

Figure 16:
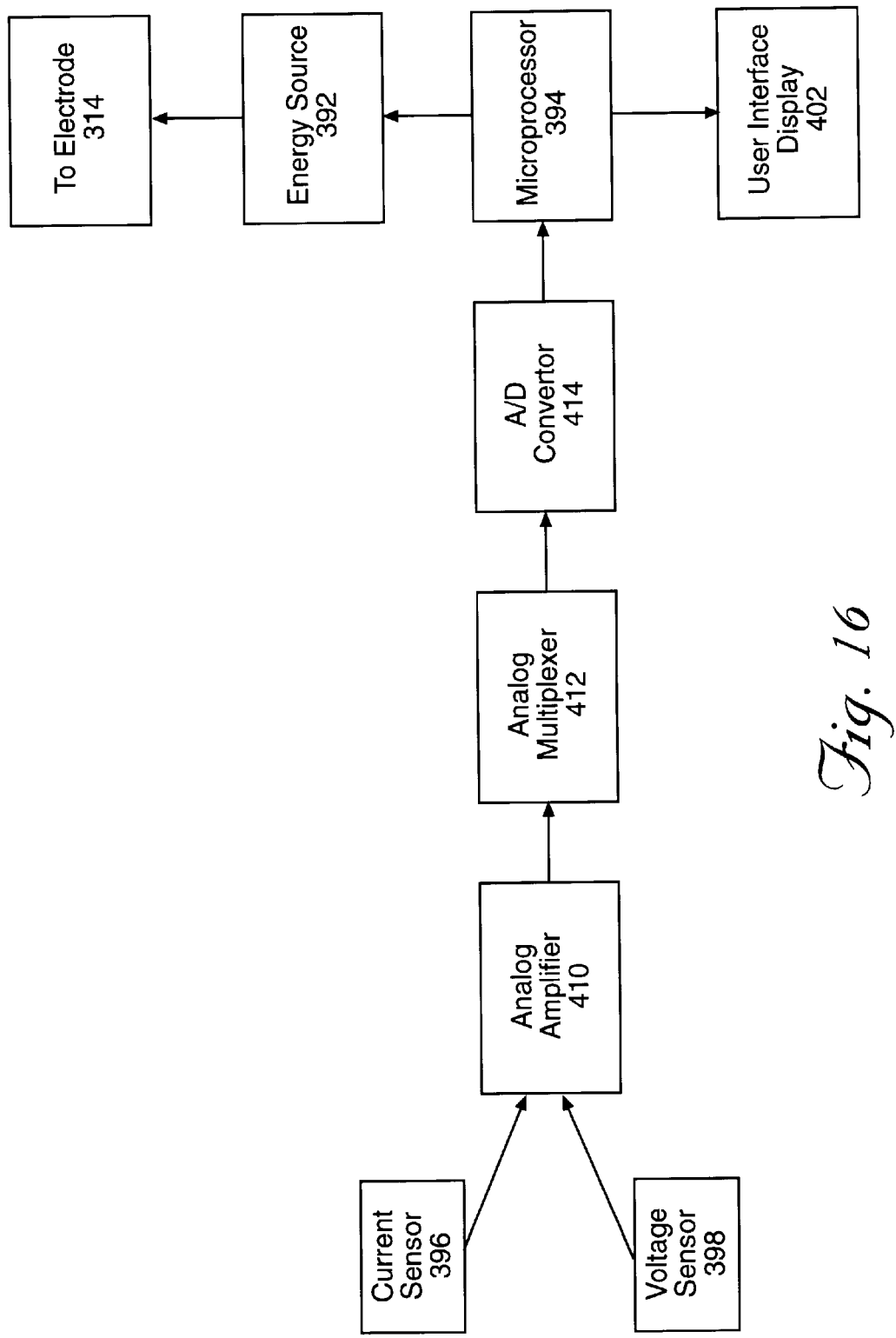
FIG. 16 depicts a block diagram of an analog amplifier, analog multiplexer and microprocessor used with the feedback control system of FIG. 15.

Referring now to FIG. 16, current sensor 396 and voltage sensor 398 are connected to the input of an analog amplifier 410. Analog amplifier 410 can be a conventional differential amplifier circuit for use with sensor 346. The output of analog amplifier 410 is sequentially connected by an analog multiplexer 412 to the input of A/D converter 414. The output of analog amplifier 410 is a voltage which represents the respective sensed temperatures. Digitized amplifier output voltages are supplied by A/D converter 414 to microprocessor 394. Microprocessor 394 may be a type 68HCII available from Motorola. However, it will be appreciated that any suitable microprocessor or general purpose digital or analog computer can be used to calculate impedance or temperature.

Microprocessor 394 sequentially receives and stores digital representations of impedance and temperature. Each digital value received by microprocessor 394 corresponds to different temperatures and impedances.

Calculated power and impedance values can be indicated on user interface and display 402. Alternatively, or in addition to the numerical indication of power or impedance, calculated impedance and power values can be compared by microprocessor 394 to power and impedance limits. When the values exceed predetermined power or impedance values, a warning can be given on user interface and display 402, and additionally, the delivery of RF energy can be reduced, modified or interrupted. A control signal from microprocessor 394 can modify the power level supplied by energy source 392.

Figure 17:
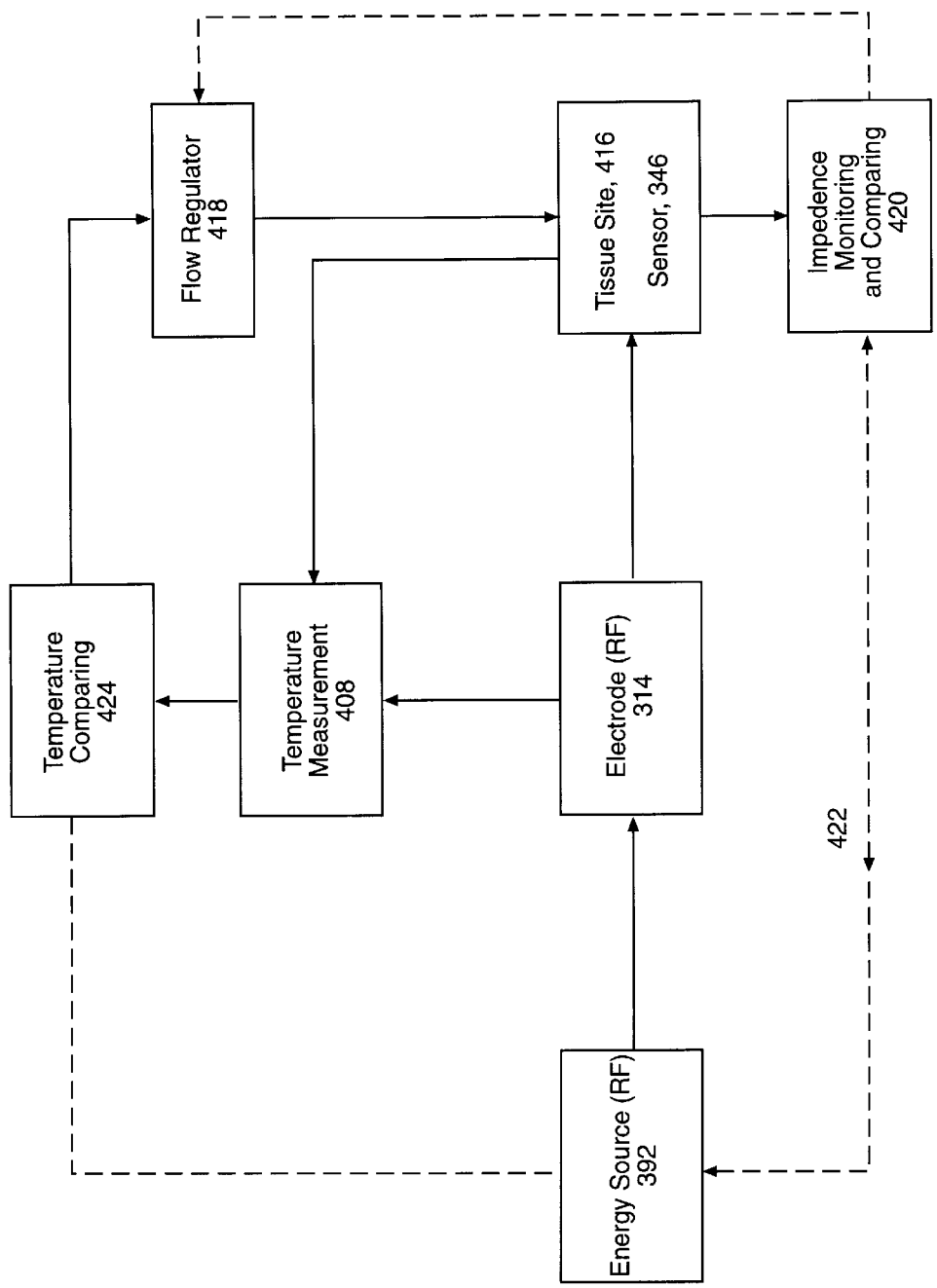
FIG. 17 depicts a block diagram of the operations performed in the feedback control system depicted in FIG. 15.

FIG. 17 illustrates a block diagram of a temperature and impedance feedback system that can be used to control the delivery of energy to tissue site 416 by energy source 392 and the delivery of cooling medium 55 to electrode 314 and/or tissue site 416 by flow regulator 418. Energy is delivered to RF electrode 314 by energy source 392, and applied to tissue site 416. A monitor 420 ascertains tissue impedance, based on the energy delivered to tissue, and compares the measured impedance value to a set value. If measured impedance is within acceptable limits, energy continues to be applied to the tissue. However if the measured impedance exceeds the set value, a disabling signal 422 is transmitted to energy source 392, ceasing further delivery of energy to RF electrode 314.

The control of cooling medium 55 to electrode 314 and/or tissue site 416 is done in the following manner. During the application of energy, temperature measurement device 408 measures the temperature of tissue site 416 and/or RF electrode 314. A comparator 424 receives a signal representative of the measured temperature and compares this value to a pre-set signal representative of the desired temperature. If the measured temperature has not exceeded the desired temperature, comparator 424 sends a signal to flow regulator 418 to maintain the cooling solution flow rate at its existing level. However if the tissue temperature is too high, comparator 424 sends a signal to a flow regulator 418 (connected to an electronically controlled micropump, not shown) representing a need for an increased cooling solution flow rate.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A method of treating a sphincter, comprising:
   providing a catheter means and an energy delivery device means coupled to the catheter means and including a tissue piercing distal end;
   introducing the catheter means into an esophagus;
   piercing a sphincter exterior surface with the energy delivery device means tissue piercing distal end;
   advancing the energy delivery device means tissue piercing distal end a sufficient distance in an interior of the sphincter to a tissue site; and
   controllably delivering energy to the tissue site and create controlled cell necrosis of the sphincter to reduce a frequency of sphincter relaxation.

2. The method of claim 1, wherein the sphincter is a lower esophageal sphincter.

3. The method of claim 1, wherein the sphincter is an upper esophageal sphincter.

4. The method of claim 2, wherein sufficient energy is applied to the lower esophageal sphincter to reduce a duration of lower esophageal sphincter relaxation.

5. The method of claim 2, wherein sufficient energy is applied to the lower esophageal sphincter to reduce a frequency of reflux of stomach contents into an esophagus.

6. The method of claim 2, wherein sufficient energy is applied to the lower esophageal sphincter to reduce a frequency of a symptom of reflux of stomach contents into an esophagus.

7. The method of claim 2, wherein sufficient energy is applied to the lower esophageal sphincter to reduce an incidence of a sequela of reflux of stomach contents into an esophagus.

8. The method of claim 2, wherein energy delivered to the sphincter produces the desired tissue effect without creating a permanent impairment of the sphincter's ability to achieve a physiologically normal state of closure.

9. The method of claim 1, wherein sufficient energy is delivered to the sphincter to cause a proliferation of fibroblast cells in the sphincter.

10. The method of claim 1, wherein sufficient energy is delivered to the sphincter to cause a proliferation of myofibroblast cells in the sphincter.

11. The method of claim 1, wherein the energy delivery device means delivers sufficient energy to create a tightening of the sphincter without permanently damaging anatomical structures near the sphincter.

12. The method of claim 1, wherein the energy delivery device means delivers sufficient energy to a lower esophageal sphincter without permanently disrupting an aorta positioned near the lower esophageal sphincter.

13. The method of claim 1, wherein the energy delivery device means delivers a sufficient amount of energy to a lower esophageal sphincter without permanently damaging a vagus nerve positioned near the lower esophageal sphincter.

14. The method of claim 1, wherein the energy delivery device means delivers a sufficient amount of energy to a lower esophageal sphincter without permanently damaging an esophageal plexus of nerves and veins positioned near the lower esophagal sphincter.

15. The method of claim 1, wherein the energy delivery device means delivers a sufficient amount of energy to a lower esophageal sphincter while preserving a blood supply to the lower esophageal sphincter.

16. The method of claim 1, wherein the energy delivery device means delivers a sufficient amount of energy to the sphincter to create submucosal lesions in the sphincter.

17. The method of claim 1, wherein the energy delivery device means includes an RF electrode means.

18. The method of claim 1, wherein the energy delivery device means includes a microwave antenna means.

19. The method of claim 1, wherein the energy delivery device means includes a waveguide means.

20. The method of claim 1, wherein the energy delivery device means includes an acoustical transducer means.

21. The method of claim 1, wherein the energy delivery device means includes a resistive heating device means.

22. The method of claim 1, wherein the energy delivery device means is delivered to the sphincter transorally without an endoscope means.

23. The method of claim 1, wherein the energy delivery device means is delivered to the sphincter with an endoscope means.

24. A method of treating a sphincter, comprising:
providing a catheter means and an energy delivery device means coupled to the catheter means, the energy delivery device means including an energy delivery surface means sized to be positioned on a tissue surface of the sphincter;
introducing the catheter means into an esophagus;
positioning the energy delivery surface means on the tissue surface of the sphincter; and
controllably delivering energy to the sphincter and create controlled cell necrosis of the sphincter to reduce a frequency of sphincter relaxation.

25. The method of claim 24, wherein the sphincter is a lower esophageal sphincter.

26. The method of claim 24, wherein the sphincter is an upper esophageal sphincter.

27. The method of claim 25, wherein sufficient energy is applied to the lower esophageal sphincter to reduce a duration of lower esophageal sphincter relaxation.

28. The method of claim 25, wherein sufficient energy is applied to the lower esophageal sphincter to reduce a frequency of reflux of stomach contents into an esophagus.

29. The method of claim 25, wherein sufficient energy is applied to the lower esophageal sphincter to reduce a frequency of a symptom of reflux of stomach contents into an esophagus.

30. The method of claim 25, wherein sufficient energy is applied to the lower esophageal sphincter to reduce an incidence of a sequela of reflux of stomach contents into an esophagus.

31. The method of claim 25, wherein energy delivered to the sphincter produces the desired tissue effect without creating a permanent impairment of the sphincter's ability to achieve a physiologically normal state of closure.

32. The method of claim 24, wherein sufficient energy is delivered to the sphincter to cause a proliferation of fibroblast cells in the sphincter.

33. The method of claim 24, wherein sufficient energy is delivered to the sphincter to cause a proliferation of myofibroblast cells in the sphincter.

34. The method of claim 24, wherein the energy delivery device means delivers sufficient energy to create a tightening of the sphincter without permanently damaging anatomical structures near the sphincter.

35. The method of claim 24, wherein the energy delivery device means delivers sufficient energy to a lower esophageal sphincter without permanently disrupting an aorta positioned near the lower esophageal sphincter.

36. The method of claim 24, wherein the energy delivery device means delivers a sufficient amount of energy to a lower esophageal sphincter without permanently damaging a vagus nerve positioned near the lower esophageal sphincter.

37. The method of claim 24, wherein the energy delivery device means delivers a sufficient amount of energy to a lower esophageal sphincter without permanently damaging an esophageal plexus of nerves and veins positioned near the lower esophageal sphincter.

38. The method of claim 24, wherein the energy delivery device means delivers a sufficient amount of energy to a lower esophageal sphincter while preserving a blood supply to the lower esophageal sphincter.

39. The method of claim 24, wherein the energy delivery device means delivers a sufficient amount of energy to the sphincter to create submucosal lesions in the sphincter.

40. The method of claim 24, wherein the energy delivery device means includes an RF electrode means.

41. The method of claim 24, wherein the energy delivery device means includes a microwave antenna means.

42. The method of claim 24, wherein the energy delivery device means includes a waveguide means.

43. The method of claim 24, wherein the energy delivery device means includes an acoustical transducer means.

44. The method of claim 24, wherein the energy delivery device means includes a resistive heating device means.

45. The method of claim 24, wherein the energy delivery device means is delivered to the sphincter transorally without an endoscope means.

46. The method of claim 24, wherein the energy delivery device means is delivered to the sphincter with an endoscope means.

47. A method of treating a sphincter, comprising:
providing a catheter means and an energy delivery device means coupled to the catheter means, the energy delivery device means including an energy delivery surface means sized to be distanced from a tissue surface of the sphincter while controllably delivering energy to the sphincter;
introducing the catheter means into an esophagus;
distancing the energy delivery surface means from a selected tissue surface of the sphincter; and
controllably delivering energy to the sphincter and creating controlled cell necrosis of the sphincter to reduce a frequency of sphincter relaxation.

48. The method of claim 47, wherein the sphincter is a lower esophageal sphincter.

49. The method of claim 47, wherein the sphincter is an upper esophageal sphincter.

50. The method of claim 48, wherein sufficient energy is applied to the lower esophageal sphincter to reduce a duration of lower esophageal sphincter relaxation.

51. The method of claim 48, wherein sufficient energy is applied to the lower esophageal sphincter to reduce a frequency of reflux of stomach contents into an esophagus.

52. The method of claim 48, wherein sufficient energy is applied to the lower esophageal sphincter to reduce a frequency of a symptom of reflux of stomach contents into an esophagus.

53. The method of claim 48, wherein sufficient energy is applied to the lower esophageal sphincter to reduce an incidence of a sequela of reflux of stomach contents into an esophagus.

54. The method of claim 48, wherein energy delivered to the sphincter produces the desired tissue effect without creating a permanent impairment of the sphincter's ability to achieve a physiologically normal state of closure.

55. The method of claim 47, wherein sufficient energy is delivered to the sphincter to cause a proliferation of fibroblast cells in the sphincter.

56. The method of claim 47, wherein sufficient energy is delivered to the sphincter to cause a proliferation of myofibroblast cells in the sphincter.

57. The method of claim 47, wherein the energy delivery device means delivers sufficient energy to create a tightening of the sphincter without permanently damaging anatomical structures near the sphincter.

58. The method of claim 47, wherein the energy delivery device means delivers sufficient energy to a lower esophageal sphincter without permanently disrupting an aorta positioned near the lower esophageal sphincter.

59. The method of claim 47, wherein the energy delivery device means delivers a sufficient amount of energy to a lower esophageal sphincter without permanently damaging a vagus nerve positioned near the lower esophageal sphincter.

60. The method of claim 47, wherein the energy delivery device means delivers a sufficient amount of energy to a lower esophageal sphincter without permanently damaging an esophageal plexus of nerves and veins positioned near the lower esophageal sphincter.

61. The method of claim 47, wherein the energy delivery device means delivers a sufficient amount of energy to a lower esophageal sphincter while preserving a blood supply to the lower esophageal sphincter.

62. The method of claim 47, wherein the energy delivery device means delivers a sufficient amount of energy to the sphincter to create submucosal lesions in the sphincter.

63. The method of claim 47, wherein the energy delivery device means includes an RF electrode means.

64. The method of claim 47, wherein the energy delivery device means includes a microwave antenna means.

65. The method of claim 47, wherein the energy delivery device means includes a waveguide means.

66. The method of claim 47, wherein the energy delivery device means includes an acoustical transducer means.

67. The method of claim 47, wherein the energy delivery device means includes a resistive heating device means.

68. The method of claim 47, wherein the energy delivery device means is delivered to the sphincter transorally without an endoscope means.

69. The method of claim 47, wherein the energy delivery device means is delivered to the sphincter with an endoscope means.

* * * * *

UNITED STATES PATENT AND TRADEMARK OFFICE
Certificate

Patent No. 6,044,846                                                                                                                                                   Patented: April 4, 2000

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Stuart D. Edwards, Portola Valley, CA; David S. Utley, San Carlos, CA; and Ronald G. Lax, Palm City, FL.

Signed and Sealed this Tenth Day of December 2002.

LINDA C. M. DVORAK
                                                                                                                                               *Supervisory Patent Examiner*
                                                                                                                                                    Art Unit 3739